(12) United States Patent
Langley et al.

(10) Patent No.: US 8,491,941 B1
(45) Date of Patent: Jul. 23, 2013

(54) RASH TREATMENT WITH SCAR PREVENTION

(75) Inventors: Wendy S. Langley, Albany, OR (US); John Mark Christensen, Corvallis, OR (US); Vernon W. Smith, Albany, OR (US); Larry M. Burris, Albany, OR (US); Steven D. Smith, Corvallis, OR (US)

(73) Assignee: Tec Laboratories, Inc., Albany, OR (US)

( * ) Notice: Subject to any disclaimer, the term of this patent is extended or adjusted under 35 U.S.C. 154(b) by 0 days.

(21) Appl. No.: 13/356,052

(22) Filed: Jan. 23, 2012

Related U.S. Application Data

(60) Provisional application No. 61/435,887, filed on Jan. 25, 2011.

(51) Int. Cl.
*A01N 65/00* (2009.01)

(52) U.S. Cl.
USPC .......................................................... 424/725

(58) Field of Classification Search
None
See application file for complete search history.

(56) References Cited

U.S. PATENT DOCUMENTS

2007/0025963 A1 2/2007 Liu
2009/0143333 A1 6/2009 Palefsky

OTHER PUBLICATIONS

REPAIR Tissue Repair Cream web page [online] [retrieved on Jan. 12, 2011], Retrieved from www.csirendayspa.com.
Homeopathic Stop Rash web page [online] [retrieved on Jan. 13, 2011], www.truerenewal.com.

*Primary Examiner* — Michael Meller

(57) ABSTRACT

Disclosed is a composition and methods of use for treating and preventing the scarring of skin rashes. When used, the composition of the invention effectively relieves itching, promotes healing, and prevents scarring of skin rashes and irritations. The composition of the invention may be applied as a spray, foam, or gel.

1 Claim, No Drawings

RASH TREATMENT WITH SCAR PREVENTION

CROSS-REFERENCE TO RELATED APPLICATIONS

None.

FEDERALLY SPONSORED RESEARCH OR DEVELOPMENT

None.

SEQUENCE LISTING

None.

BACKGROUND OF THE INVENTION

The present invention is in the technical field of skin care products. More particularly, the present invention is in the technical field of skin rash treatment and scar prevention products.

Significant skin rashes, such as those caused by contact allergens such as poison ivy, oak, or sumac, those caused by contact irritants, and rashes caused by the environment such as prickly heat rash frequently lead to scarring. Scarring caused by severe rashes, especially those caused by contact allergens, can result in loss of feeling and/or movement of the affected area and cause cosmetic concerns, which could be permanent. Rashes itch, and when scratched, can further damage the injured tissue and also lead to infection which can cause even worse scarring.

Products currently on the market address scars by way of reducing the appearance of existing scar tissue. These products cannot be used while the wound is healing and are to be used after the wound has fully healed. Other products treat and/or prevent scars resulting from cuts or burns, but not skin rashes in particular. There remains a need for a treatment to prevent scar formation and reduce excessive scar formation resulting from skin rashes specifically.

BRIEF SUMMARY OF THE INVENTION

The present invention discloses compositions having healing and scar preventing capabilities and methods of use to treat various skin rashes, also known as dermatitis.

Further, the present invention is applied directly to the affected area to effectively decrease itching, heal, protect from infection and encourage healthy skin generation to prevent scar tissue from forming. The composition can be applied as a liquid spray, foam, or formulated into a gel. Further, the present invention is simply applied to the affected area as often as desired to effectively decrease itching, heal, protect from infection and encourage healthy skin generation to prevent scar tissue formation.

DETAILED DESCRIPTION OF THE INVENTION

Referring now to the invention in more detail, the composition of this invention comprises water, an alcoholic plant extract or combination of alcoholic plant extracts present in an amount effective to treat dermatitis and prevent scarring, a humectant or combination of humectants to moisturize the affected areas, a surfactant or combination of surfactants to help solubilize non-water-soluble material, a plant essence or combination of plant essences to heal and soothe the affected area, a chelating agent, green tea extract powder, an optional gelling agent or combination of gelling agents to make into an optional gel formulation, and an optional neutralizing agent to help form the optional gel.

In more detail, the alcoholic plant extract or combination of alcoholic plant extracts of the instant invention comprises at least one alcoholic extract derived from a plant or synthetic and present in an amount of about 0.00001 to about 50 weight percent. The humectant or combination of humectants of the instant invention may be selected from a variety of known and available pharmaceutically acceptable materials and present in the amount ranging from about 0.001 to about 50 weight percent. The surfactant or combination of surfactants of the instant invention may be selected from a variety of known and available pharmaceutically acceptable materials and present in the amount ranging from about 0.1 to 5 weight percent. The plant essence or combination of plant essences of the instant invention may be at least one plant essence derived from a plant or synthetic and present in an amount from about 0.01 to about 20 weight percent. The chelating agent of the instant invention may be selected from a variety of known and available pharmaceutically acceptable materials and present in the amount ranging from about 0.05 to one weight percent. The green tea extract powder may be present in the amount ranging from about 0.001 to one weight percent.

An optional gelling agent and optional neutralizing agent may be added to the combination of ingredients of the instant invention to thicken it into a gel consistency or a solid substrate. The gelling agent may be selected from a variety of known and available pharmaceutically acceptable natural or synthetic materials, as well as the neutralizing agent.

In further detail, a preferred amount of alcoholic plant extract or combination of alcoholic plant extracts present in the composition of the instant invention may range from about 0.01 to about 30 weight percent. An even more preferred amount is 8.4 weight percent. Preferred alcoholic extracts of the instant invention are at least one alcoholic extract selected from the group grindelia, plantago, calendula, heracleum, hura brasiliensis, hydrocotyle asiatica, imperatoria, jatropha, kamala, primula obconica, sprianthes, eryngium maritimum, euphorbia, ledum, helleborus, anagallis, balsamum peruvianum, phytolacca, anacardium, mezereum, rhus, and camphora. An especially preferred alcoholic plant extract or combination of alcoholic plant extracts is a combination of alcoholic extracts of grindelia robusta, plantago major, and calendula officinalis.

Furthermore, a preferred amount of humectant or combination of humectants present in the composition of the instant invention may range from about 0.5 to about 5 weight percent. An even more preferred amount is 1 weight percent. Preferred humectants of the instant invention are at least one selected from the group consisting of sorbitol, glycols, glycerins, sodium PCA, plant oils, mineral oils, shea butter, cocoa butter, petrolatum, cholesterol, silicones, animal oils, jojoba, squalene, and lanolin. An especially preferred humectant is glycerin.

A preferred amount of surfactants or combination of surfactants present in the composition of the instant invention may range from about 1 to about 3 weight percent. An even more preferred amount is 2 weight percent. Preferred surfactants of the instant invention are at least one selected from the group consisting of polyethoxylated castor oil, alcohols, alkanolamides, alkanolamines, sulfonates, alkylbenzenes, olefins, acetates, oxides, amines, sulfonates, betaines, polymers, alkylphenols, fatty acids, poloxamers, phenols, glycols, imidazolines, isothionates, lanolin, lecithin, lignin, anhydrides, methyl esters, glycerides, sulfonates, glycols, phenols, quaternary surfactants, sarcosine, silicone, soaps, sodium, sorbitan, sugars, oils, sorbates, polysorbates, octoxynols, nonyl phenyl ethoxylates, sodium lauryl sarcosinate, lanolin alcohol, and their pharmaceutically acceptable derivatives, ethers, esters, sulfates, ethoxylates, oils, extracts, and/or salts. An especially preferred surfactant is polyethoxylated castor oil.

A preferred amount of plant essence or combination of plant essences in the composition of the instant invention may range from about 0.1 to about 10 weight percent. An even more preferred amount is 1.19 weight percent. Preferred plant essences used in the composition of the instant invention may be selected from the group consisting of the essence of oregano, thyme, anise, lemongrass, tea tree (melaleuca), cinnamon bark, cinnamon leaf, eucalyptus, camphor, geranium, azalea, lavender, garlic, birch tar, sage, walnut, peppermint, menthol crystals, ginger, lemon, rosemary, clove, echinacea, geranium, rose, chrysanthemum, arnica, balm mint, birch, burdock root, calendula, chamomile, cucumber, green tea, jojoba, licorice root, sunflower, aloe vera, comphrey, gumweed, ginger, lemongrass, guava, eucalyptus, willow herb, capsicum, cinnamon, grapefruit seed, olive leaf, St. John's wort, goldenseal, and their pharmaceutically acceptable extracts, oils, and/or salts. An especially preferred plant essence or combination of plant essences is a combination of tea tree oil, thyme oil, and menthol crystals.

A preferred amount of chelating agent in the composition of the instant invention may range from about 0.1 to 0.5 weight percent. An even more preferred amount is 0.2 weight percent. Preferred chelating agents used in the composition of the instant invention may be selected from the group consisting of ethylenediamine, ethylenediaminetetraacetic acid, dimercaprol, diethylenetriaminepentaacetic acid porphyrins, triglycollamic acid, vitamin B-12, citric acid, and their pharmaceutically acceptable salts. An especially preferred chelating agent is disodium ethylenediaminetetraacetic acid (EDTA).

A preferred amount of green tea extract powder in the composition of the instant invention may range from about 0.005 to about 0.05 weight percent. An even more preferred amount is 0.01 weight percent.

Several liquid formulations have been formulated with combinations of the various ingredients listed above. A preferred formulation contains 10 weight percent glycerin, 1 weight percent calendula officinalis 10% tincture, 2 weight percent polyethoxylated castor oil, 1 weight percent tea tree oil, 0.1 weight percent thyme oil, 0.09 weight percent menthol crystals, 0.1 weight percent plantago major 10% tincture, 1 weight percent grindelia robusta 10% tincture, 1 weight percent additional alcohol, 0.2 weight percent disodium ethylenediaminetetraacetic acid (EDTA), 0.01 weight percent green tea extract powder, and QS purified water equaling 55.6 weight percent. The ingredients are added to a mixing vessel in the order given and mixed until uniform.

This invention also includes several methods of use. One method of use is as a liquid application that can be sprayed on the affected area several times a day and/or as often as necessary to stop itching, prevent infection and aid in healing to prevent scar formation. The composition of the instant invention is housed in any type of container providing a spray application. The composition of the invention is then sprayed onto the affected skin of the afflicted individual until wet but not dripping. The composition is left on the area to air dry, during which time it eases itching and aids in healing to prevent scar formation. The treated area composition may be then covered with a bandage, if desired.

Another method of use is as a foam application. The liquid composition of the instant invention is housed in any type of container providing a foaming pump applicator. The composition of the invention is applied to the affected area as a foam. The composition may be rubbed to spread onto the skin. The composition is left on the area to air dry, during which time it stops itching, heals the tissue, and prevents scar formation. The treated area may then be covered with a bandage, if desired.

Further, another method of use is to apply the composition of the instant invention to any means of bandage or dressing. The application is such that the composition of the invention is sprayed, dipped into, or otherwise applied to the bandage or dressing until it is wet with the composition, but not to the point of dripping. The bandage or dressing is then placed on the affected area and left in place until it is dry, or longer if the affected individual prefers, to stop the itch and aid in healing and prevent scar formation.

Another method of use is to apply the composition of the instant invention as a gel to the affected area to stop itching, heal and prevent scar formation of the affected area without dripping.

Accordingly, besides the advantages of the compositions and methods described in this specification, several advantages of one or more aspects include, without limitation:
a) To provide novel methods for treating and preventing scarring of all forms of skin rashes or dermatitis.
b) To provide prolonged, multi-stage action in treating rashes.
c) To provide a rash treatment that prevents scars that can be applied any time during or after the healing process.
d) To provide a treatment that also prevents scars that doesn't require the user to wait until after the wound has closed or rash has healed in order to use it.
e) To provide a treatment in which all ingredients are GRAS for their intended purpose.
f) To provide a treatment and scar prevention product that is pleasant to use.
g) To provide treatment and scar prevention that is not greasy like silicone based products.
h) To provide treatment and scar prevention that is also cooling and soothing.
i) To provide a treatment for rashes that relieves pain, itching, inflammation and promotes healthy wound healing while preventing scar formation.
j) To provide treatment and scar prevention with an easy, no-touch application.
k) To provide treatment and scar prevention that relieves pain and violent itching of hot, burning, irritated and/or inflamed skin and rashes due to poison oak, poison ivy, poison sumac, prickly heat rash, hives, insect bites, minor cuts, scrapes and burns.
l) To provide treatment and scar prevention that protects, cools, and soothes rashes and minor skin irritations.
m) To provide a rash treatment and anti-itch product that also promotes healing to prevent scar tissue formation.
n) To provide a product that encourages healthy skin growth.
o) To provide a product that prevents scarring of poison plant dermatitis.
p) To provide a product that prevents scarring from minor burns.
q) To provide a product that treats and prevents scarring of rashes that can be used by the entire family.
r) To provide a product that promotes healthy skin generation.

s) To provide a product for rash treatment and scar prevention that is easy, not complicated.
t) To provide a product prevents scarring of rashes that contains no enzymes.
u) To provide an FDA compliant homeopathic drug that is not subject to regulatory action.
v) To provide a product that repairs damaged skin to prevent scarring while healing and relieving the pain and itch of rashes.

In broad embodiment, the present invention is a liquid or gel composition to treat and prevent scar formation when applied directly to skin rashes.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:

1. A composition consisting essentially of 0.01 wt % to 30 weight % of a mixture of alcoholic extracts of grindelia robusta, plantago major and calendula officinalis.

* * * * *